United States Patent
Giordano et al.

(10) Patent No.: US 6,588,277 B2
(45) Date of Patent: Jul. 8, 2003

(54) METHOD FOR DETECTING TRANSVERSE MODE VIBRATIONS IN AN ULTRASONIC HAND PIECE/BLADE

(75) Inventors: James R. Giordano, Milford, OH (US); Foster B. Stulen, Mason, OH (US)

(73) Assignee: Ethicon Endo-Surgery, Cincinnati, OH (US)

( * ) Notice: Subject to any disclaimer, the term of this patent is extended or adjusted under 35 U.S.C. 154(b) by 0 days.

(21) Appl. No.: 09/861,870

(22) Filed: May 21, 2001

(65) Prior Publication Data

US 2002/0170357 A1 Nov. 21, 2002

(51) Int. Cl.$^7$ .......................... G01N 29/04; A61B 17/32
(52) U.S. Cl. ............................. 73/579; 73/649; 73/659; 606/169
(58) Field of Search ................. 73/579, 649, 650, 73/659, 432.1; 606/169

(56) References Cited

U.S. PATENT DOCUMENTS

| | | | |
|---|---|---|---|
| 2,917,691 A | 12/1959 | DePrisco et al. ........... 318/118 |
| 3,809,870 A | * 5/1974 | Auble et al. ................... 702/34 |
| 3,868,625 A | * 2/1975 | Speigner et al. ............ 340/626 |
| 4,584,875 A | * 4/1986 | Woo et al. ..................... 57/264 |
| 4,922,902 A | 5/1990 | Wuchinich et al. ........... 604/22 |
| 5,001,649 A | 3/1991 | Lo et al. ..................... 364/484 |
| 5,026,387 A | 6/1991 | Thomas ....................... 606/169 |
| 5,112,300 A | 5/1992 | Ureche ......................... 604/22 |
| 5,151,085 A | 9/1992 | Sakurai et al. ................ 604/22 |
| 5,180,363 A | 1/1993 | Idemoto et al. ............... 202/32 |
| 5,191,796 A | * 3/1993 | Kishi et al. .................. 310/336 |
| 5,400,267 A | 3/1995 | Denen et al. ................ 364/552 |
| 5,406,503 A | 4/1995 | Williams, Jr. et al. ...... 702/106 |
| 5,425,704 A | 6/1995 | Sakurai et al. ................ 604/22 |
| 5,449,370 A | 9/1995 | Vaitekunas ................... 606/169 |
| 5,630,420 A | 5/1997 | Vaitekunas ............. 128/662.03 |
| 5,707,369 A | 1/1998 | Vaitekunas et al. ........... 606/31 |
| 5,776,155 A | * 7/1998 | Beaupre et al. ................ 604/22 |
| 5,879,364 A | 3/1999 | Bromfield et al. .......... 606/169 |
| 5,968,007 A | 10/1999 | Simon et al. .................. 604/22 |
| 6,017,354 A | 1/2000 | Culp et al. ................... 606/170 |
| 6,019,775 A | 2/2000 | Sakurai ....................... 606/169 |
| 6,066,135 A | 5/2000 | Honda .......................... 606/39 |
| 6,090,123 A | 7/2000 | Culp et al. ................... 606/180 |
| 6,391,042 B1 | * 5/2002 | Cimino ......................... 604/22 |
| 6,425,906 B1 | * 7/2002 | Young et al. ................ 606/169 |
| 6,432,118 B1 | * 8/2002 | Messerly ..................... 606/169 |

FOREIGN PATENT DOCUMENTS

WO    WO-00/51508    9/2000

OTHER PUBLICATIONS

US 2001/0034532A1, Ultrasonic cutting and coagulation knife using transverse vibrations, Cimino, Oct. 25, 2001.*
US 2002/0052616 A1, Wiener et al. Method for detecting transverse vibrations in an ultrasonic hand piece.*

* cited by examiner

Primary Examiner—Helen Kwok
Assistant Examiner—Jacques M Saint-Surin
(74) Attorney, Agent, or Firm—Darby & Darby (57) ABSTRACT

A method for detecting transverse mode vibrations in an ultrasonic hand piece/blade for determining the existence of unwanted vibration in the hand piece/blade. A tracking filter centered at the drive frequency of the generator, is used to monitor the drive frequency of the ultrasonic generator and attenuate the drive signal when it exceeds a predetermined level. The tracking filter has a wide pass band. Alternatively, a tracking filter having a pass band which is divided into several regions is used to avoid other longitudinal resonances, such as a resonance at a second harmonic, or other spectral features that would otherwise detract from the tracking accuracy of the filter.

22 Claims, 6 Drawing Sheets

METHOD FOR DETECTING TRANSVERSE MODE VIBRATIONS IN AN ULTRASONIC HAND PIECE/BLADE

BACKGROUND OF THE INVENTION

1. Field of the Invention

The present invention generally relates to ultrasonic surgical systems and, more particularly, to a method for detecting transverse vibrations in an ultrasonic hand piece/blade.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

Another problem associated with the prior art ultrasonic systems is unwanted vibrations in the hand piece/blade. Ultrasonic blades also vibrate along an axis which is perpendicular to the longitudinal axis of vibration of the hand piece/blade. Such vibrations are called transverse mode vibrations. If the longitudinal vibration is considered to be in the Z direction is an X, Y, Z coordinate system, vibrations along a Y-axis of the blade are called transverse "flap mode" vibrations and vibrations along an X-axis of the blade are called transverse "hook mode" vibrations. Blades typically have a sheath surrounding their blade part. Excess transverse mode vibrations generate heat which can lead to high blade sheath temperatures. Such excessive heat can also heat the blade and cause damage to tissue surrounding the narrow zone of coagulation, which can adversely affect patient healing and recovery time. In addition, transverse mode vibrations can also cause blade tip failures. The vibrations may also be indicative of defects in the hand piece, such as damaged transducer disks. While excess transverse mode vibrations are often audible, too often a user will ignore them until the ultrasonic generator can no longer drive the hand piece/blade. It is therefore advantageous to detect transverse mode vibrations to prevent undesired effects, such as tissue damage which can occur from an over heated blade.

SUMMARY OF THE INVENTION

The invention is a method for detecting transverse mode vibrations in an ultrasonic hand piece/blade. A tracking filter centered at the drive frequency of the generator, is used to monitor the drive frequency of the ultrasonic generator and attenuate the drive signal when it exceeds a predetermined level. The tracking filter has a wide pass band. Alternatively, a tracking filter having a pass band which is divided into several regions is used to avoid other longitudinal resonances, such as a resonance at a second harmonic, or other spectral features that would otherwise detract from the tracking accuracy of the filter. In an embodiment of the invention, the tracking filter is implemented using a notch filter or a combination of a notch filer and a band pass filter. In the preferred embodiment, notch filter or the band pass filter are either analog adaptive filters, such as switching-capacitive filters, or digital filters, such as a finite impulse response (FIR) filters or infinite impulse (IIR) filters, or the like.

In accordance with the invention, an output level, such as the rms value, of a filter located in a current sense circuit or a voltage sense circuit is monitored to determine whether the output exceeds a predetermined threshold level for any given blade. In the preferred embodiment, the filter is located in the voltage sense circuit. If the rms value of the notch filter exceeds the predetermined level, then the hand piece/blade contains transverse mode vibrations. Alternatively, the rate of change with respect to load of the rms value is used to indicate whether a blade is on the verge of exhibiting transverse behavior or whether any transverse behavior is rendering the blade unsuitable for use.

In an embodiment of the invention, the ratio of multiple notch filters to each other is used to determine whether a blade contains off-frequence transverse modes. Alternatively, the ratio of the output level of the notch filter to the input drive signal level is used to indicate whether transverse mode behavior is present in the hand piece/blade.

In a further embodiment of the invention, the predetermined threshold level is set based on a blade ID code stored in the connector which connects the hand piece to the ultra sonic generator.

The method provides automatic detection of off-resonance transverse mode vibrations in an ultrasonic hand piece/blade. Moreover, the method permits the easy identification of bad hand pieces and/or blades. As a result, patient safety and recuperation time are increased due to the reduction of damage to tissue surrounding the narrow area of coagulation. In addition, the method, avoids the costs associated with adding an FFT analyzer to the software/hardware of the generator to perform frequency sweeps to detect transverse modes.

BRIEF DESCRIPTION OF THE DRAWINGS

The foregoing and other advantages and features of the invention will become more apparent from the detailed description of the preferred embodiments of the invention given below with reference to the accompanying drawings in which.

DESCRIPTION OF ILLUSTRATIVE EXEMPLARY EMBODIMENTS

Figure 1:
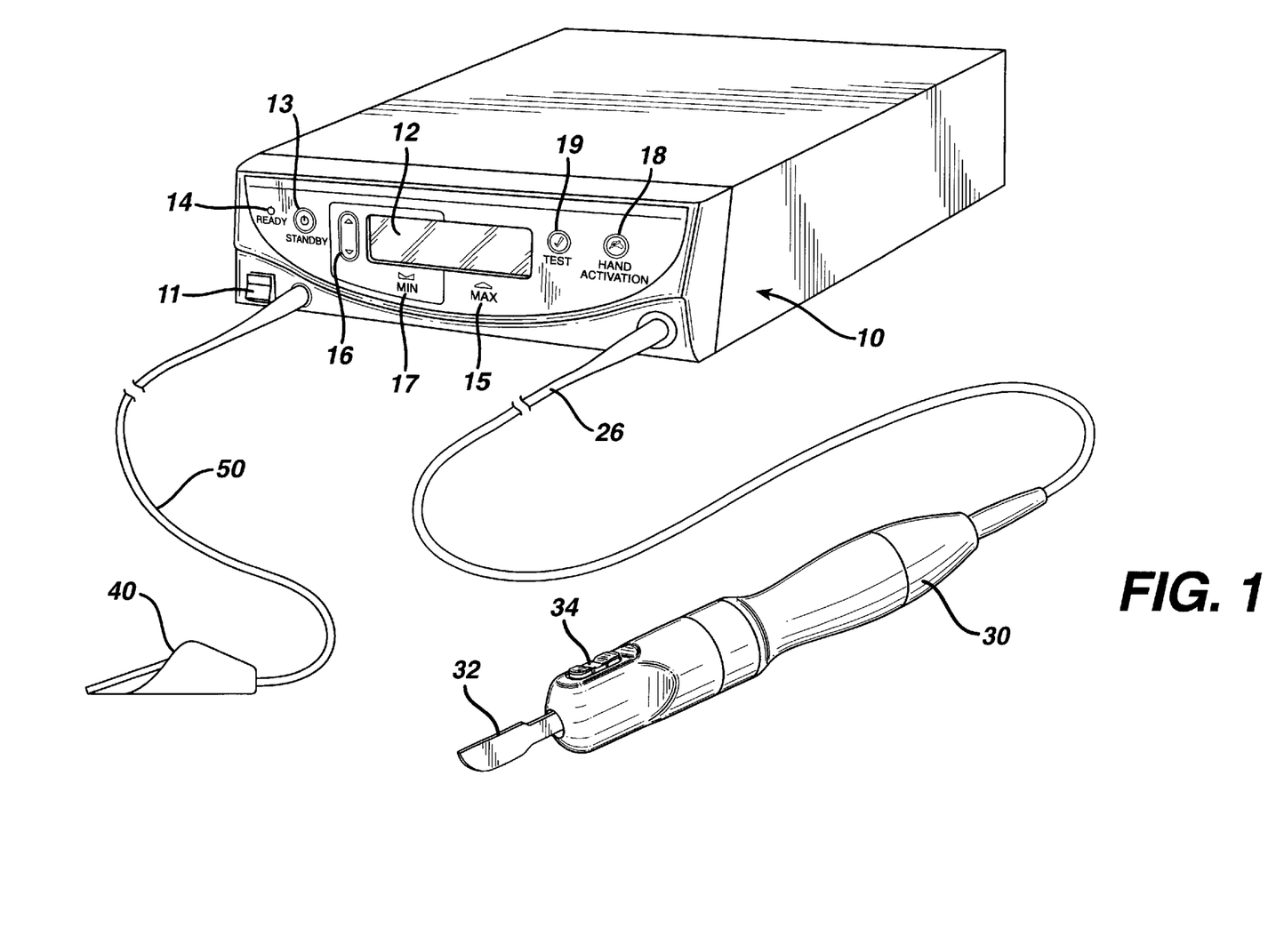
FIG. 1 is an illustration of a console for an ultrasonic surgical cutting and hemostasis system, as well as a hand piece and foot switch in which the method of the present invention is implemented.

FIG. 1 is an illustration of a system for implementing the method in accordance with the invention. By means of a first set of wires in cable 20, electrical energy, i.e., drive current, is sent from the console 10 to a hand piece 30 where it imparts ultrasonic longitudinal movement to a surgical device, such as a blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 20. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. When powered up, the "standby" light 13 is illuminated. To toggle to ready mode, depress button 13. When it is ready for operation, the "ready" indicator 14 is illuminated and the standby light goes out. If the unit is to supply maximum power, the MAX button 15 is depressed. If a lesser power is desired, the MIN button 17 is activated. This automatically deactivates the MAX button. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
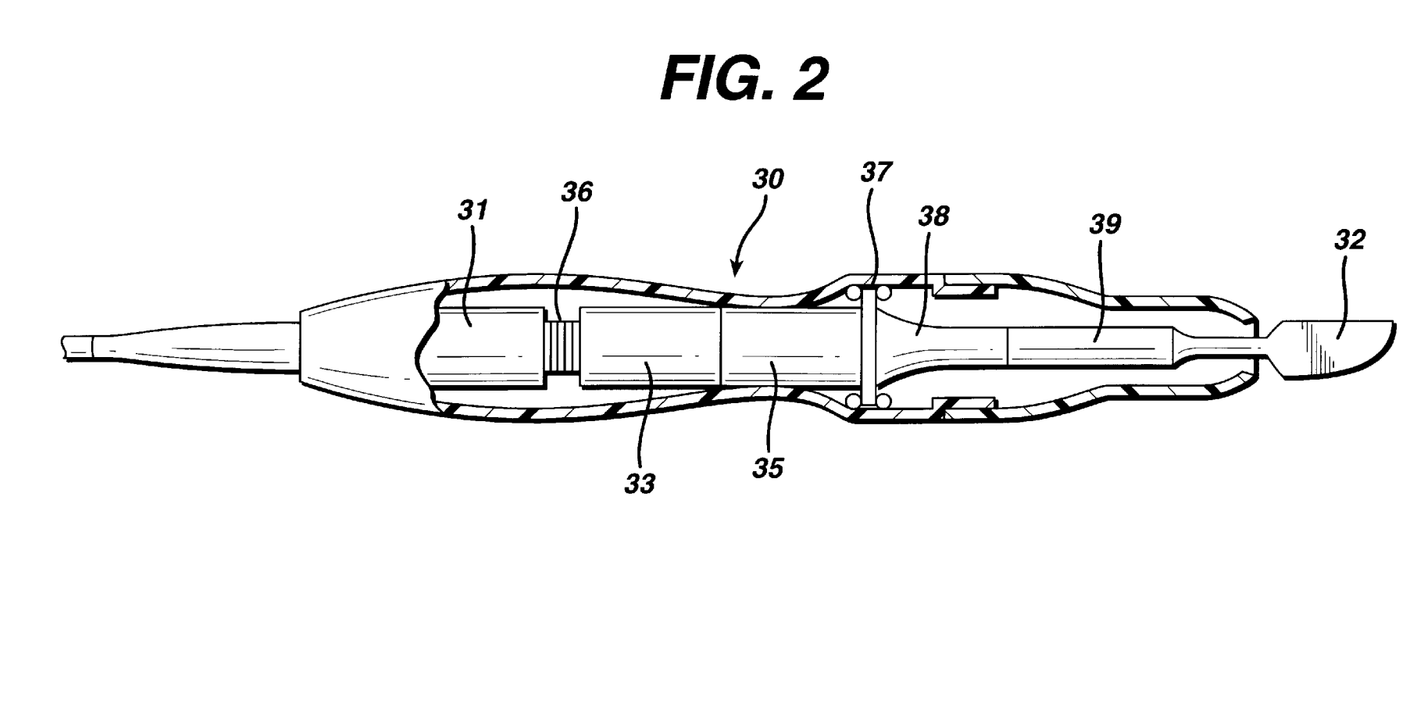
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a current of about 380 mA RMS at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
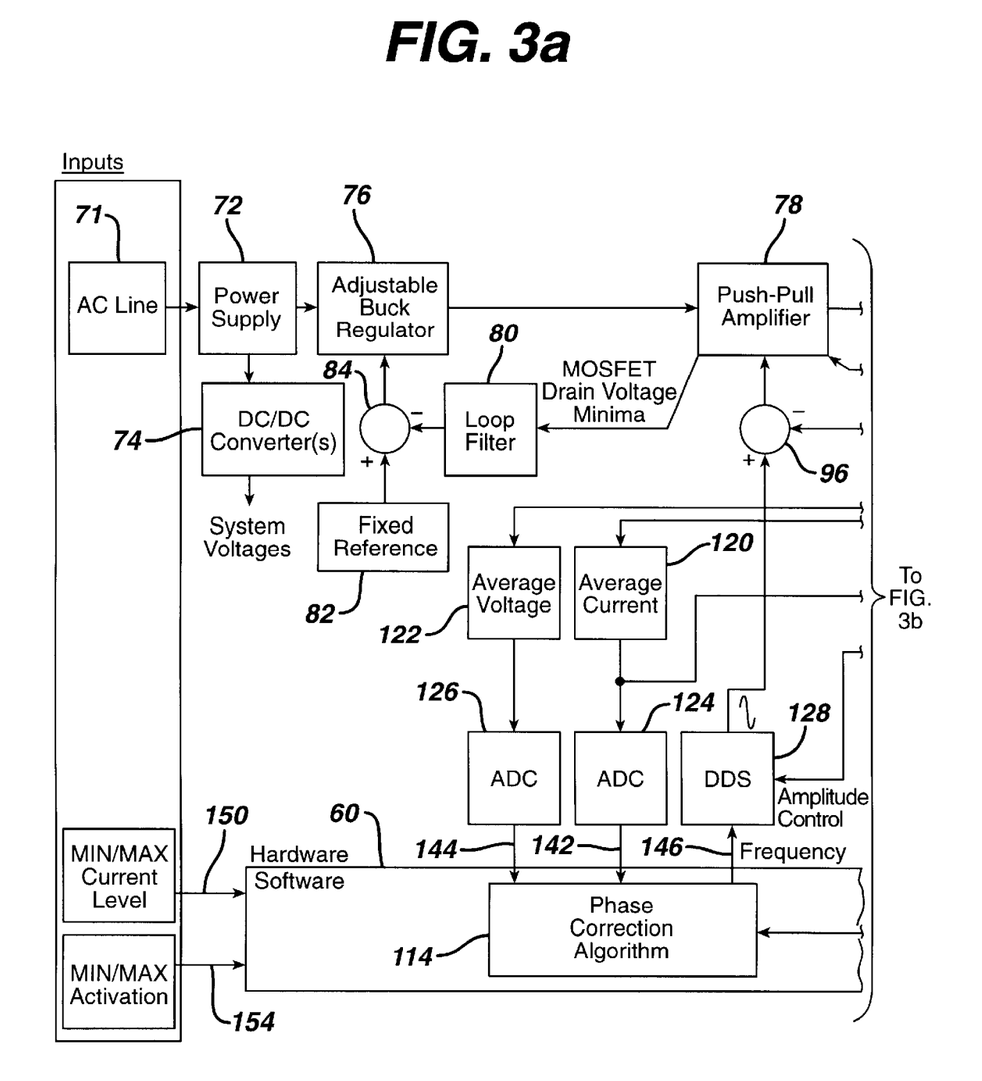
FIGS. 3(a) and 3(b) are block diagrams illustrating an ultrasonic generator for implementing the method of the present invention.
Figure 3B:
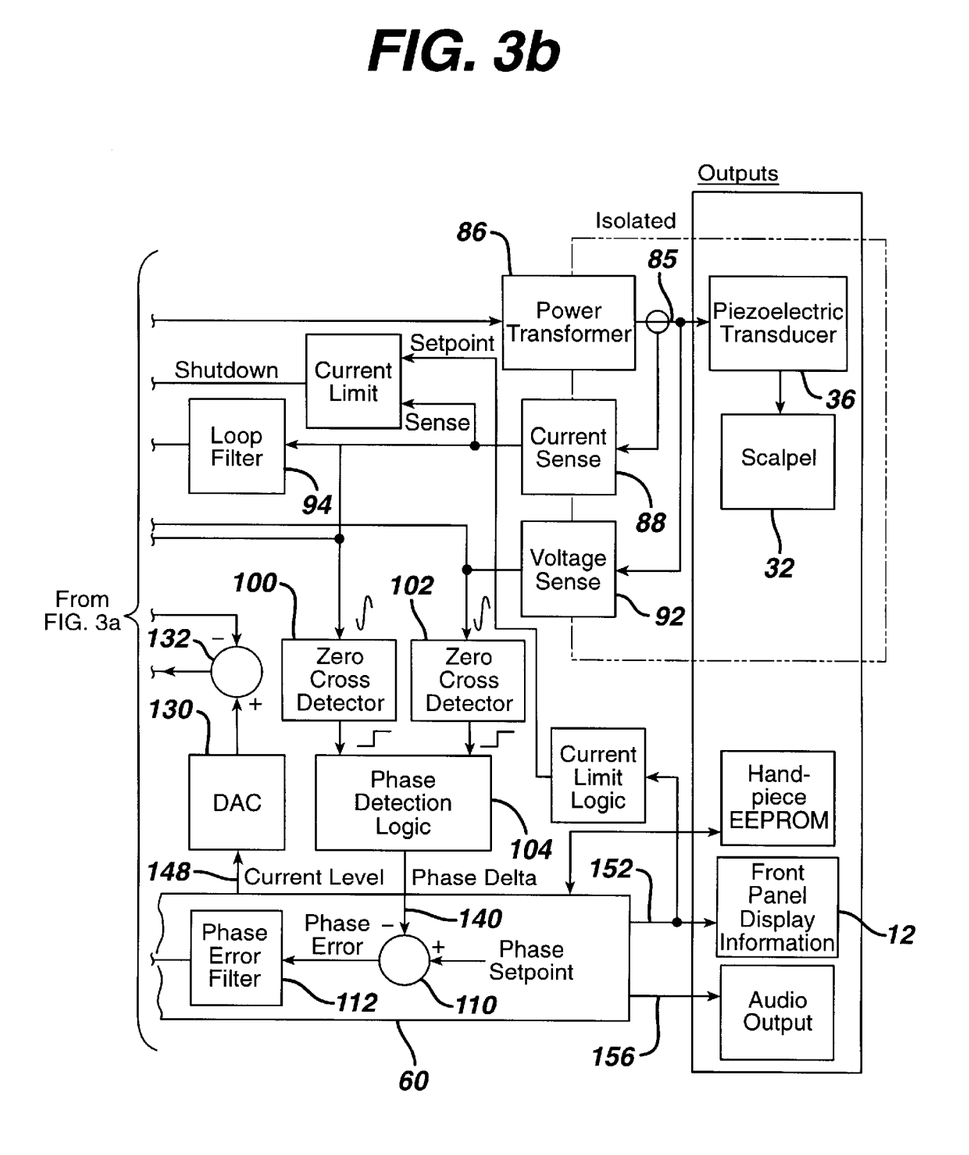

The system which creates the ultrasonic electrical signal for driving the transducer in the hand piece is illustrated in FIGS. 3(a) and 3(b). This drive system is flexible and can create a drive signal at a desired frequency and power level setting. A DSP 60 or microprocessor in the system is used for monitoring the appropriate power parameters and vibratory frequency as well as for causing the appropriate power level to be provided in either the cutting or coagulation operating modes. The DSP 60 or microprocessor also stores computer programs which are used to perform diagnostic tests on components of the system, such as the hand piece/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(b)) to the console front panel display 12.

To actually cause the surgical blade to vibrate, the user activates the foot switch 40 or the hand piece switch 34. This activation puts a signal on line 154 in FIG. 3(a). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

In order to obtain the impedance measurements and phase measurements, the DSP 60 and the other circuit elements of FIGS. 3(a) and 3(b) are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 104, which represents the difference in phase between the current and voltage. The size of this phase difference is also an indication of resonance. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

Figure 4:
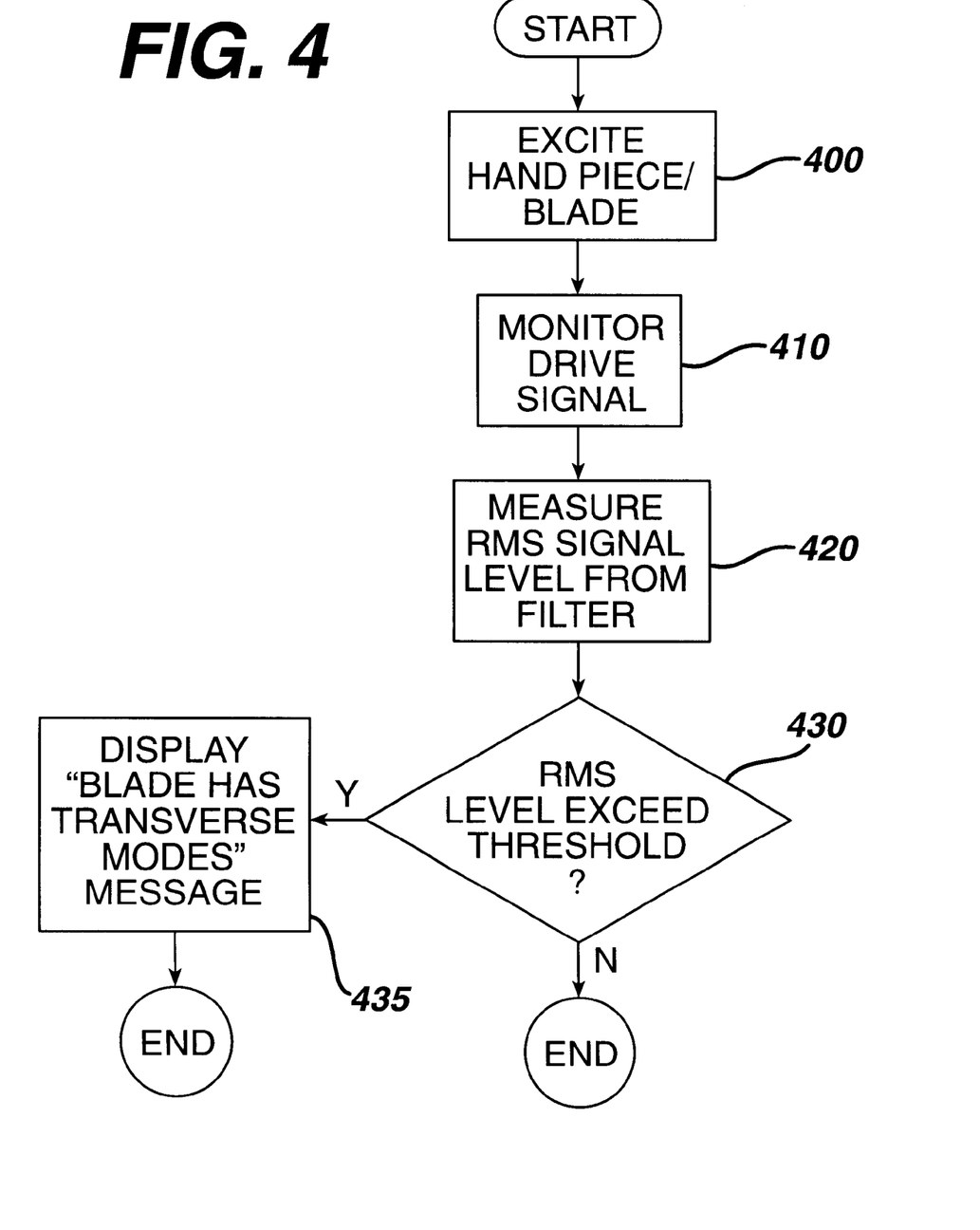
FIG. 4 is flow chart illustrating a preferred embodiment of the method of the invention.

FIG. 4 is a flow chart illustrating a preferred embodiment of the invention. Under the control of the program stored in the DSP or microprocessor 60 shown in FIGS. 3(a) and 3(b), the method of the invention is implemented by using the ultrasonic generator to excite the hand piece/blade, as indicated in step 400. In the preferred embodiment, the drive signal is an ultrasonic signal having a current range of 200–400 ma, and a frequency of 55.5 kHz.

Next, the change over time as a result of load and temperature of the drive signal is monitored, i.e., tracked, by a filter located in current sense circuit 88 or a voltage sense circuit 92 (see FIG. 3(b)) to detect whether a significant amount of off-frequency transverse mode vibrations have occurred, as indicated in step 410. In the preferred embodiment, the filter is located in the voltage sense circuit 92. The output signal from the filter is measured, as indicated in step 420. The level of the measured output signal is compared to a predetermined threshold, as indicated in step 430. In an embodiment of the invention, the filter is a notch filter or a combination of a notch filter and a band pass filter. In a preferred embodiment, the notch filter and band pass filter are either analog adaptive filters, such as switching-capacitive filters, or digital filters, such as finite impulse response (FIR) filters or infinite impulse (IIR) filters. If the level of the output signal exceeds the predetermined level, then the hand piece/blade contains off-frequency resonance modes and a "Blade Has Transverse Modes" message is displayed on an LCD located on the ultrasonic generator, as indicated in step 435.

In an alternative embodiment, the ratio of a rms level of the output signal from a combination of the notch filter and band pass filter is measured. This measured rms signal ratio is compared to the predetermined threshold. In the preferred embodiment, the predetermined threshold is approximately −20 db.

Figure 5:
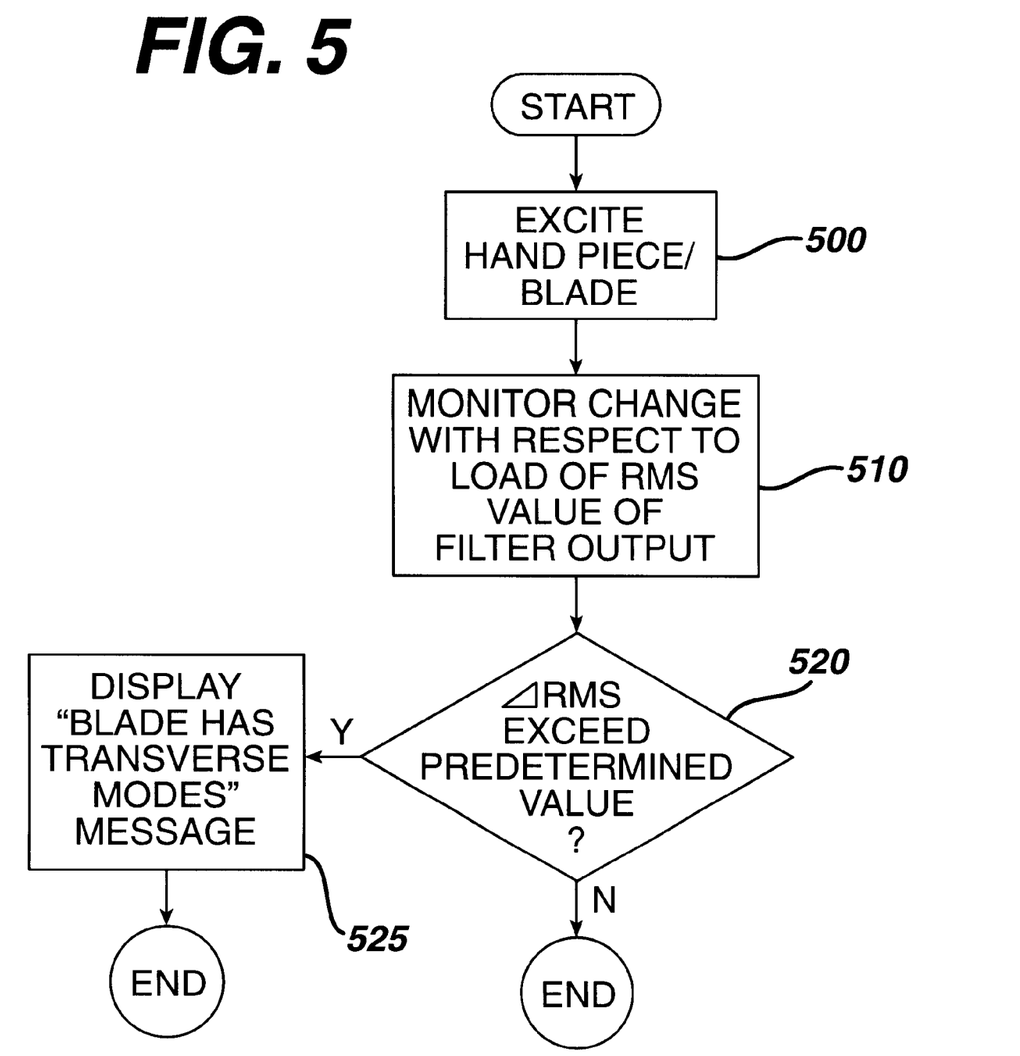
FIG. 5 is a flow chart illustrating an alternative embodiment of the invention.

FIG. 5 is a flow chart illustrating an alternative embodiment of the invention. Under the control of the program stored in the DSP or microprocessor 60 shown in FIGS. 3(a) and 3(b), the ultrasonic generator is used to excite the hand piece/blade, as indicated in step 500. In the preferred embodiment, the drive signal is an ultrasonic signal having a current range of 200–400 ma, and a frequency of 55.5 kHz.

The rate of change with respect to load of the rms value of an output signal from the filter is continuously monitored, as indicated in step 510. The change in the level of the rms value of the output signal from the filter is used to indicate whether a blade is about to exhibit transverse behavior or whether any transverse behavior is rendering the blade unsuitable for use. Alternatively, the change with respect to load in the level of the rms value of the output of the filter is detected at start up (i.e., each time the blade is activated). In an embodiment of the invention, the filter is a notch filter or a combination of a notch filter and a band pass filter. In a preferred embodiment, the notch filter and band pass filter are either analog adaptive filters, such as switching-capacitive filters, or digital filters, such as finite impulse response (FIR) filters or infinite impulse (IIR) filters.

The rate of change with respect to load of the measured rms value is compared to a predetermined value, as indicated in step 520. If the rate of change for an increasing load is greater than a predetermined value, then the hand piece/blade is about to exhibit transverse behavior, or it contains transverse mode vibrations which render the blade inappropriate for use, and a "Blade Has Transverse Modes" message is displayed on the LCD, as indicated in step 530. In an embodiment of the invention, the predetermined level for a notch filter and band pass filter combination greater than zero.

In an embodiment of the invention, a ratio of multiple band pass filters to each other is used to determine whether a blade contains off-frequencey transverse modes. Alternatively, the ratio of the output level of the band pass filter to the input drive signal level is used to indicate whether transverse mode behavior is present.

In another embodiment, more than one notch filter is used to monitor the output of the filter. In this case, the output rms levels of the multiple filters are measured and compared to the predetermined level. If the rms level exceed the predetermined level, then transverse mode behavior is present.

In a further embodiment of the invention, the predetermined threshold level is set based on a blade ID code stored in the connector which connects the hand piece to the ultrasonic generator.

Using the method, automatic detection of transverse mode vibrations in an ultrasonic hand piece/blade vibrations is achieved. An easy identification of bad hand pieces and/or blades is also achieved. The method provides increase of patient safety and patient healing times due to the reduction of damage to tissue surrounding the narrow area of coagulation.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A method for detecting transverse vibrations in an ultrasonic hand piece/blade, comprising:
   applying a drive signal to the hand piece/blade using an ultrasonic generator;
   monitoring a change over time of the drive signal;
   measuring a level of an output signal from a filter located in the ultrasonic generator;
   comparing the output signal to a predetermined level; and
   if the output signal exceeds the predetermined level, displaying a message on a liquid crystal display of the generator to indicate that the ultrasonic hand piece/blade contains transverse vibrations.

2. The method of claim 1, wherein said monitoring step comprises the step of:
   tracking the drive signal to determine whether a significant amount of off-frequency transverse mode vibrations have occurred.

3. The method of claim 2, wherein said tracking step is performed using at least one of a notch filter and a band pass filter.

4. The method of claim 3, wherein the at least one of the notch filter and the band pass filter are one of an analog filter and a digital filter.

5. The method of claim 4, wherein the analog filter is a switching-capacitive filter and the digital filter is one of a finite impulse response filter and an infinite impulse filter.

6. The method of claim 1, wherein said tracking is performed via at least one of a notch filter and a band pass filter.

7. The method of claim 6, wherein the notch filter and the band pass filter are one of an analog filter and a digital filter.

8. The method of claim 7, wherein the analog filter is a switching-capacitive filter and the digital filter is one of a finite impulse response filter and an infinite impulse filter.

9. The method of claim 1, wherein the predetermined level is greater than zero.

10. The method of claim 1, wherein the step of displaying the message comprises the step of:
    displaying a "Blade Has Transverse Modes" message on the liquid crystal display.

11. The method of claim 1, wherein the drive signal is applied at a frequency of approximately 55.5 kHz and a current in the range of approximately 200 to 400 ma.

12. A method for detecting transverse vibrations in an ultrasonic hand piece/blade, comprising:
    applying a drive signal to the hand piece/blade using an ultrasonic generator;
    monitoring a change with respect to load of a rms value of an output signal from a filter;
    comparing the change with respect to load of the rms value output from the filter to a predetermined level; and
    displaying a message on a display, if the rms value exceeds the predetermined level to indicate that the ultrasonic hand piece/blade contains transverse vibrations.

13. The method of claim 12, wherein said monitoring step comprises the step of:
    tracking the drive signal to determine whether a significant amount of off-frequency transverse mode vibrations have occurred.

14. The method of claim 13, wherein said tracking step is performed using at least one of a notch filter and a band pass filter.

15. The method of claim 14, wherein the notch filter and band pass filter are one of an analog filter and a digital filter.

16. The method of claim 13, wherein the analog filter is a switching-capacitive filter and the digital filter is one of a finite impulse response filter and an infinite impulse filter.

17. The method of claim 12, wherein said tracking step is performed using at least one of the notch filter and the band pass filter.

18. The method of claim 17, wherein the notch filter and the band pass filter are one of an analog filter and a digital filter.

19. The method of claim 18, wherein the analog filter is a switching-capacitive filter and the digital filter is one of a finite impulse response filter and an infinite impulse filter.

20. The method of claim 12, wherein the predetermined level is greater than zero.

21. The method of claim 12, wherein the step of displaying the message comprises the step of:
    displaying a "Blade Has Transverse Modes" message on the liquid crystal display.

22. The method of claim 12, wherein the drive signal is applied at a frequency of approximately 55.5 kHz and a current in the range of approximately 200 to 400 ma.

* * * * *